(12) United States Patent
Ellsworth et al.

(10) Patent No.: US 9,656,274 B2
(45) Date of Patent: *May 23, 2017

(54) BLOOD COMPONENTS SEPARATOR DISK

(71) Applicant: Harvest Technologies Corporation, Lakewood, CO (US)

(72) Inventors: James R. Ellsworth, Marshfield, MA (US); Steven F. Levesque, North Pembroke, MA (US)

(73) Assignee: Harvest Technologies Corporation, Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/207,009

(22) Filed: Jul. 11, 2016

(65) Prior Publication Data

US 2017/0008012 A1  Jan. 12, 2017

Related U.S. Application Data

(60) Continuation of application No. 14/750,412, filed on Jun. 25, 2015, now Pat. No. 9,393,576, which is a
(Continued)

(51) Int. Cl.
| | |
|---|---|
| *A61M 1/36* | (2006.01) |
| *B04B 7/12* | (2006.01) |
| *B01D 17/02* | (2006.01) |
| *B01D 21/24* | (2006.01) |
| *B01L 3/00* | (2006.01) |

(Continued)

(52) U.S. Cl.
CPC .............. *B04B 7/12* (2013.01); *A61M 1/3693* (2013.01); *B01D 17/0217* (2013.01); *B01D 21/2433* (2013.01); *B01D 21/262* (2013.01); *B01L 3/5021* (2013.01); *B01L 3/50215* (2013.01); *B04B 7/00* (2013.01); *B04B 11/00* (2013.01); *G01N 33/491* (2013.01); *A61M 1/029* (2013.01); *B01D 2221/10* (2013.01); *B01L 2300/0803* (2013.01); *B01L 2300/0832* (2013.01)

(58) Field of Classification Search
CPC ................................................... A61M 1/3693
USPC ...... 210/513–516, 518; 494/37, 85; 220/216
See application file for complete search history.

(56) References Cited

U.S. PATENT DOCUMENTS

| | | |
|---|---|---|
| 10,140 A | 10/1853 | Thompson, Jr. |
| 280,820 A | 7/1883 | Hickson |
(Continued)

FOREIGN PATENT DOCUMENTS

| | | |
|---|---|---|
| DE | 89 10 591 | 12/1989 |
| DE | 89 10 591.5 | 12/1989 |
(Continued)

OTHER PUBLICATIONS

Order Construing the Terms of U.S. Pat. No. 7,077,273 and RE43,547, DE 65, Filed Sep. 22, 2014.
(Continued)

*Primary Examiner* — David Sorkin
(74) *Attorney, Agent, or Firm* — Fish & Richardson P.C.

(57) ABSTRACT

A separator disk for use in centrifugal separation of components is designed to automatically position itself during separation at the interface between the supernatant and the remaining components. Preferably the interface is between plasma and red blood cells.

9 Claims, 4 Drawing Sheets

Related U.S. Application Data division of application No. 14/160,809, filed on Jan. 22, 2014, now Pat. No. 9,393,575, which is a continuation of application No. 13/680,350, filed on Nov. 19, 2012, now abandoned, which is a continuation of application No. 12/453,577, filed on May 15, 2009, now abandoned, which is a division of application No. 11/206,869, filed on Aug. 19, 2005, now Pat. No. 7,547,272, which is a division of application No. 10/019,680, filed as application No. PCT/US01/11732 on Apr. 27, 2001, now Pat. No. 7,077,273.

(60) Provisional application No. 60/200,150, filed on Apr. 28, 2000.

(51) Int. Cl.

| | | |
|---|---|---|
| B04B 7/00 | (2006.01) | |
| B04B 11/00 | (2006.01) | |
| B01D 21/26 | (2006.01) | |
| G01N 33/49 | (2006.01) | |
| A61M 1/02 | (2006.01) | |

(56) References Cited

U.S. PATENT DOCUMENTS

| | | |
|---|---|---|
| 593,333 A | 11/1897 | Park |
| 1,818,924 A | 8/1931 | Basmadjian |
| 3,256,977 A | 6/1966 | Petterson |
| 3,409,165 A | 11/1968 | Creith |
| 3,508,653 A | 4/1970 | Coleman |
| 3,618,810 A | 11/1971 | Wilson |
| 3,647,070 A | 3/1972 | Adler |
| 3,661,265 A | 5/1972 | Greenspan |
| 3,814,248 A | 6/1974 | Lawhead |
| 3,814,258 A | 6/1974 | Ayres |
| 3,852,194 A | 12/1974 | Zine |
| 3,887,466 A | 6/1975 | Ayres |
| 3,894,950 A | 7/1975 | Ayres |
| 3,894,951 A | 7/1975 | Ayres |
| 3,894,952 A | 7/1975 | Ayres |
| 3,897,337 A | 7/1975 | Ayres |
| 3,897,343 A | 7/1975 | Ayres |
| 3,897,940 A | 8/1975 | Gele |
| 3,909,419 A | 9/1975 | Ayres |
| 3,919,085 A | 11/1975 | Ayres |
| 3,920,557 A | 11/1975 | Ayres |
| 3,929,646 A | 12/1975 | Adler |
| 3,931,010 A | 1/1976 | Ayres |
| 3,931,018 A | 1/1976 | North |
| 3,931,928 A | 1/1976 | Kido |
| 3,935,113 A | 1/1976 | Ayres |
| 3,941,699 A | 3/1976 | Ayres |
| 3,945,928 A | 3/1976 | Ayres |
| 3,951,801 A | 4/1976 | Ayres |
| 3,957,654 A | 5/1976 | Ayres |
| 3,972,812 A | 8/1976 | Gresl, Jr. |
| 4,001,122 A | 1/1977 | Griffin |
| 4,055,501 A | 10/1977 | Cornell |
| 4,083,788 A | 4/1978 | Ferrara |
| 4,088,582 A | 5/1978 | Murty et al. |
| 4,152,270 A | 5/1979 | Cornell |
| 4,154,690 A | 5/1979 | Ballies |
| 4,169,060 A | 9/1979 | Columbus |
| 4,180,465 A | 12/1979 | Murty |
| 4,279,863 A | 7/1981 | Friehler |
| 4,294,707 A | 10/1981 | Ikeda et al. |
| 4,310,430 A | 1/1982 | Ichikawa |
| 4,364,832 A | 12/1982 | Ballies et al. |
| 4,369,117 A | 1/1983 | White |
| 4,417,981 A | 11/1983 | Nugent |
| 4,443,345 A | 4/1984 | Wells |
| 4,487,700 A | 12/1984 | Kanter |
| 4,492,634 A | 1/1985 | Villa-Real |
| 4,563,332 A | 1/1986 | Mitchell et al. |
| 4,588,556 A | 5/1986 | Sarstedt |
| 4,608,178 A | 8/1986 | Johansson et al. |
| 4,707,276 A | 11/1987 | Dodge et al. |
| 4,751,001 A | 6/1988 | Saunders |
| 4,818,386 A | 4/1989 | Burns |
| 4,824,560 A | 4/1989 | Alspector |
| 4,844,818 A | 7/1989 | Smith |
| 4,853,137 A | 8/1989 | Ersson |
| 4,877,520 A | 10/1989 | Burns |
| 4,946,601 A | 8/1990 | Fiehler |
| 4,954,264 A | 9/1990 | Smith |
| 5,053,134 A | 10/1991 | Luderer et al. |
| 5,282,981 A | 2/1994 | Adams et al. |
| 5,314,074 A | 5/1994 | Inbar et al. |
| 5,316,779 A | 5/1994 | Morey |
| 5,389,265 A | 2/1995 | Luoma, II |
| 5,393,674 A | 2/1995 | Levine et al. |
| 5,454,958 A | 10/1995 | Fiehler |
| 5,456,885 A | 10/1995 | Coleman et al. |
| 5,533,518 A | 7/1996 | Vogler |
| 5,552,325 A | 9/1996 | Nochumson |
| 5,560,830 A | 10/1996 | Coleman |
| 5,577,513 A | 11/1996 | Van Vlasselaer |
| 5,632,895 A | 5/1997 | Tsukagoshi |
| 5,632,905 A | 5/1997 | Haynes |
| 5,707,331 A | 1/1998 | Wells |
| 5,707,876 A | 1/1998 | Levine |
| 5,736,033 A | 4/1998 | Coleman et al. |
| 5,785,925 A | 7/1998 | U'Ren |
| 5,840,502 A | 11/1998 | Van Vlasselaer |
| 5,860,937 A | 1/1999 | Cohen |
| 5,889,584 A | 3/1999 | Wardlaw |
| 5,918,622 A | 7/1999 | Perez |
| 6,280,400 B1 | 8/2001 | Niermann |
| 6,641,517 B2 | 11/2003 | Anderson |
| 7,077,273 B2 | 7/2006 | Ellsworth et al. |
| 7,547,272 B2 | 6/2009 | Ellsworth et al. |
| RE43,547 E | 7/2012 | Ellsworth et al. |
| 9,393,575 B2 * | 7/2016 | Ellsworth ........... A61M 1/3693 |
| 9,393,576 B2 * | 7/2016 | Ellsworth ........... A61M 1/3693 |

FOREIGN PATENT DOCUMENTS

| | | |
|---|---|---|
| EP | 1 106 252 | 6/2001 |
| EP | 1 129 779 | 9/2001 |
| JP | S64-044850 | 12/1981 |
| JP | S56-168814 | 2/1989 |
| JP | 52-126613 | 10/1997 |
| WO | WO 79/00135 | 3/1979 |
| WO | 79/00135 | 3/1989 |

OTHER PUBLICATIONS

Robert E. Marx et al., "Platelet-rich plasma. Growth factor enhancement for bone grafts", Oral and Maxillofacial Surgery, University of Miami School of Medicine, Jan. 1998.
Complaint for Patent Infringement, DE 1, 1-1-1-3 (Exhibits A-C), Filed Oct. 24, 2012.
Report to the PTO, DE 3, Filed Oct. 24, 2012.
Amended Complaint for Patent Infringement, DE 5, 5-1 (Exhibits A-E), Filed Feb. 15, 2013.
Celling Technologies, LLC's Answer, Defenses, and Counterclaims to Plaintiffs Amended Complaint, DE 10, 10-1 (Exhibit A), Filed Apr. 11, 2013.
Defendant Thermogenesis Corp.'s Answer, Defenses, and Counterclaims to Plaintiffs Amended Complaint, DE 12, 12-1 (Exhibit A), Filed Apr. 11, 2013.
Second Amended Complaint for Patent Infringement, DE 32, 32-1 (Exhibit A-E) Filed Jan. 10, 2014.
Amended Report to the PTO, DE 35, Filed Jan. 13, 2014.
Defendant Thermogenesis Corp.'s Answer, Defenses, and Counterclaims to Plaintiff's Second Amended Complaint, DE 37, Filed Feb. 28, 2014.
Celling Technologies, LLC's Answer, Defenses, and Counterclaims to Plaintiffs Second Amended Complaint, DE 38, Filed Feb. 28, 2014.

(56) References Cited

OTHER PUBLICATIONS

Cesca's Therapeutics Inc., and Celling Technologies, LLC's Response to Plaintiff Harvest Technologies Corporation's First Set of Joint Interrogatories to Defendants Cesca Therapeutics Inc. and Celling Technologies, LLC (Nos. 1-6), May 1, 2014.
Joint Claim Chart, DE 49, 49-1, Filed May 21, 2014.
Defendants Cesca's and Ceiling's Opening Claim Construction Brief, De 50, Filed May 30, 2014 33. Harvest Technologies Corporation's Opening Claim Construction Brief, DE 51, Filed May 30, 2014.
Amended Joint Claim Chart, DE 52, 52-1 (Exhibit A), Filed Jun. 9, 2014.
Defendants Cesca's and Ceiling's Answering Claim Construction Brief, DE 54, Filed Jun. 27, 2014.
Harvest Technologies Corporation's Answering Claim Construction Brief, DE 55, Filed Jun. 27, 2014.
Joint Appendix of Intrinsic Evidence, DE 56, 56-1-56-22, Filed Jun. 27, 2014.
Harvest Markman Hearing Transcript, DE 58, Jul. 9, 2014.
Cesca Therapeutics Inc.'s First Supplemental Responses to Plaintiff Harvest Technologies Corporation's First Set of JT Interrogatories to Defendants Cesca Therapeutics Inc. and Celling Technologies, LLC (Nos. 1-6) (Appendices B01-08 and C), filed Dec. 19, 2014.
Celling Technologies, LLC's First Supplemental Responses to Plaintiff Harvest Technologies Corporation's First Set of JT Interrogatories to Defendants Cesca Therapeutics Inc. and Celling Technologies, LLC (Nos. 1-6) (Appendices B01-08) and C, filed Dec. 19, 2014.
Stipulated Motion and [Proposed] Order for Dismissal With Prejudice, filed Aug. 20, 2015, 2 pages.

\* cited by examiner

BLOOD COMPONENTS SEPARATOR DISK

CROSS-REFERENCE TO RELATED APPLICATIONS

This application is a continuation of U.S. application Ser. No. 13/680,350 filed on Nov. 19, 2012, which is a continuation of U.S. application Ser. No. 12/453,577 filed on May 15, 2009, which is a divisional of U.S. application Ser. No. 11/206,869 filed Aug. 19, 2005, now U.S. Pat. No. 7,547,272, which is a divisional of U.S. application Ser. No. 10/019,680 filed Jan. 4, 2002, now U.S. Pat. No. 7,077,273, which was the national stage of International Application No. PCT/US01/11732 filed Apr. 27, 2001, which was published in English, and claims priority of U.S. Provisional Application No. 60/200,150 filed Apr. 28, 2000.

This invention relates to methods and apparatus for use in the separation of fluids into components having different specific gravities. The invention finds particular utility in the centrifugal separation of the components of blood.

BACKGROUND

Centrifugal separation of blood into components of different specific gravities, such as red blood cells, white blood cells, platelets, and plasma is known from U.S. Pat. No. 5,707,331 (Wells). The apparatus shown in that patent employs a disposable processing tube having two chambers, and blood to be separated into components is placed in one of the chambers. The processing tube is placed in a centrifuge, which subjects the blood to centrifugal forces to separate the components. The supernatant is then automatically decanted into the second of the chambers.

To retain, principally, the red blood cells during the decant of the supernatant, the apparatus disclosed in the Wells patent includes a shelf placed in the first chamber at the expected level of the interface between the red blood cells and the less-dense components, including the plasma. One problem with the arrangement shown in the '331 Wells patent, however, is that the position of the interface varies with the particular proportions of the components (e.g., the hematocrit) of the blood to be processed. Thus, if the shelf is placed at the expected position of the interface for blood of average hematocrit, and the hematocrit of the particular blood being processed is low, the shelf will be above the interface after separation. Such a position of the shelf will hinder the flow of the components near the interface during decanting, thus retaining significant amounts of these components in the first chamber and reducing the separation efficiency of the system.

SUMMARY OF THE INVENTION

In accordance with the invention, a movable separator disk, which automatically positions itself at the interface between the separated components, is placed in the first chamber. In the preferred embodiment, the disk is capable of moving vertically and is designed to position itself automatically at the interface between red blood cells and the remaining components in the centrifugal separation of blood.

Decant of the supernatant can be either by gravity drain or by centrifugal transfer, and a main function of the disk is to restrict the flow of the component below it, e.g., red blood cells, during decant. This ensures that the supernatant is not contaminated and increases the efficiency of the process.

The invention contemplates two embodiments for the disk. In one embodiment, the disk is supported on a central shaft such that an annulus is formed between the perimeter of the disk and the interior surface of the first chamber. The dimensions of the annulus are such that the flow of red blood cells through it during decant is restricted such that they do not contaminate the decanted supernatant to any significant degree.

In another embodiment, the disk is arranged on the shaft such that, when the chamber is tilted for gravity decanting, the disk rotates such that one edge of the disk engages the wall of the chamber to block flow of red blood cells.

In either of these embodiments, the specific gravity of the disk and its shape may be chosen so that a major part of the upper surface lies just below the interface, thus facilitating release of the supernatant from the disk during decanting. This upper surface is also preferably curved to match the cylindrical shape the interface assumes during centrifugation.

DETAILED DESCRIPTION OF THE PREFERRED EMBODIMENTS

Figure 1A:
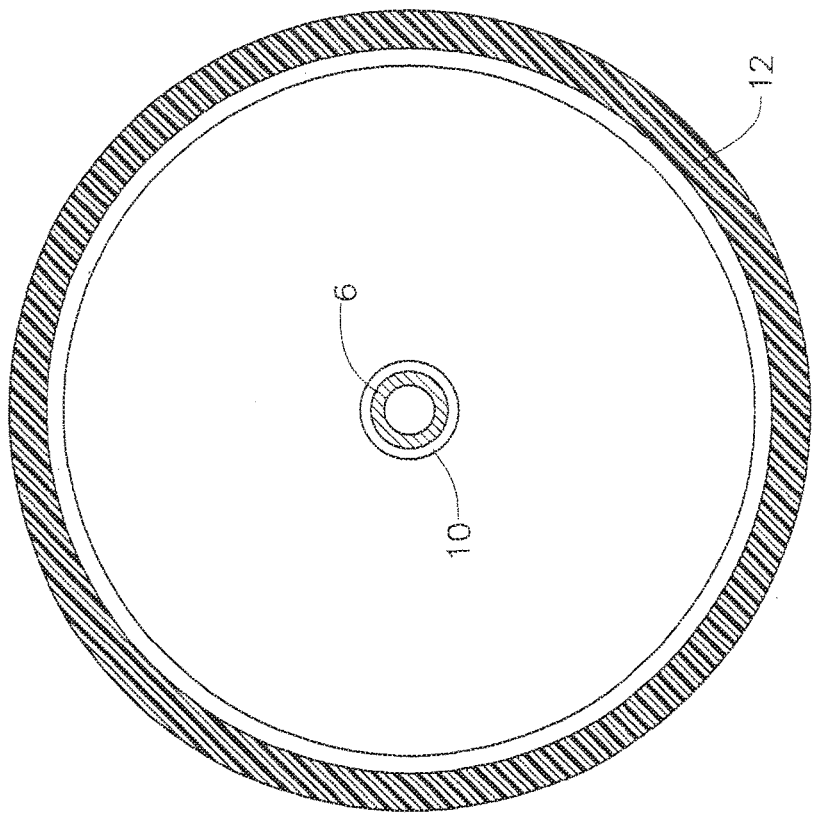
FIG. 1A is a longitudinal cross-section of a portion of a processing tube chamber and a separator disk in accordance with a first embodiment of the invention.

With reference to FIGS. 1 and 2, one chamber 2 of a processing tube, such as that shown in the '331 Wells patent has a separator disk 4 in accordance with the invention supported therein by a central shaft 6. The shaft 6 is designed to direct fluid introduced into the chamber to the bottom of the chamber. This precludes the formation of an air bubble at the bottom of the chamber, particularly when the bottom of the chamber is tapered. Thus, fluid is introduced into the chamber by inserting a cannula attached to a syringe containing blood into the shaft 6 and discharging the blood from the syringe into the chamber. A central opening 8 in the disk receives the shaft 6 in such a manner that the disk easily slides along the shaft.

The shaft 6 may not be necessary in all instances, for example, when the bottom of the processing tube is flat. In that instance the disk does not have a central hole.

The disk is preferably made of material having a specific gravity that allows the disk to float at the interface with red blood cells. In the preferred embodiment that specific gravity is about 1.04 (e.g., polystyrene), which is just less than the specific gravity of red blood cells at 70% hematocrit. Thus, when the blood is centrifuged, the disk moves to the interface between the red blood cells and the other components.

The interface will naturally assume a cylindrical shape with a cylindrical radius equal to the distance to the center of rotation of the centrifuge. The disk may be cylindrical, to match the shape of the interface.

In the embodiment shown in FIGS. 1A, 1B, 2A and 2B, the diameters of the hole 8 and the shaft 6 are such that an annular gap 10 is formed between the outer surface of the shaft and the interior surface of the hole 8. Similarly, an annular gap 12 is provided between the perimeter of the disk and the interior surface of the tube 2.

Figure 1B:
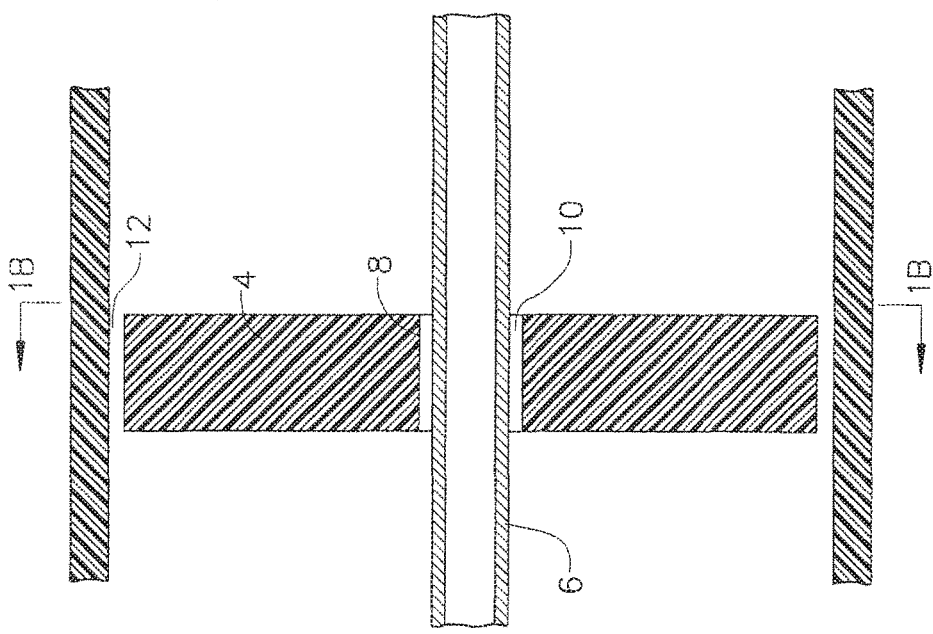
FIG. 1B is a transverse cross section taken along line 1B-1B of FIG. 1A.

FIGS. 1A and 1B illustrate the position of the disk during centrifugation, and it will be appreciated that the gaps 10 and 12 are large enough to allow passage of the descending heavier components, e.g., red blood cells and the ascending lighter components, e.g., plasma. According to this embodiment, however, the diameter of the central opening 8 is large enough whereby during decanting the disk 4 rotates as shown in the figures.

Figure 2A:
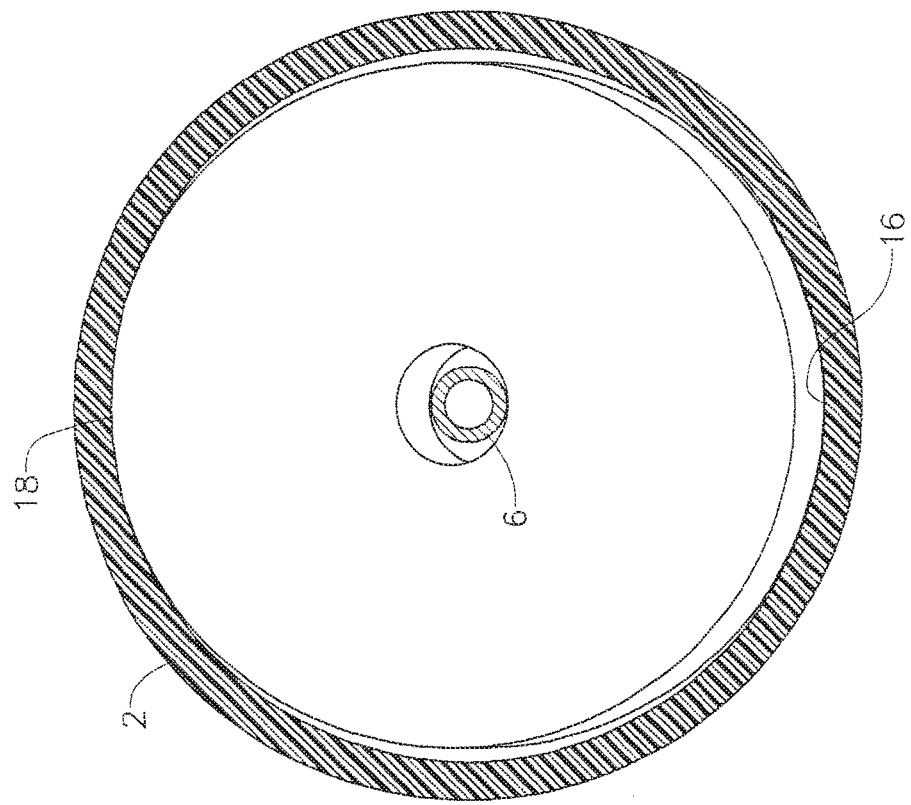
FIG. 2A is a longitudinal cross-section of the embodiment of FIGS. 1A and 1B when the separator disk is tilted during decanting.
Figure 2B:
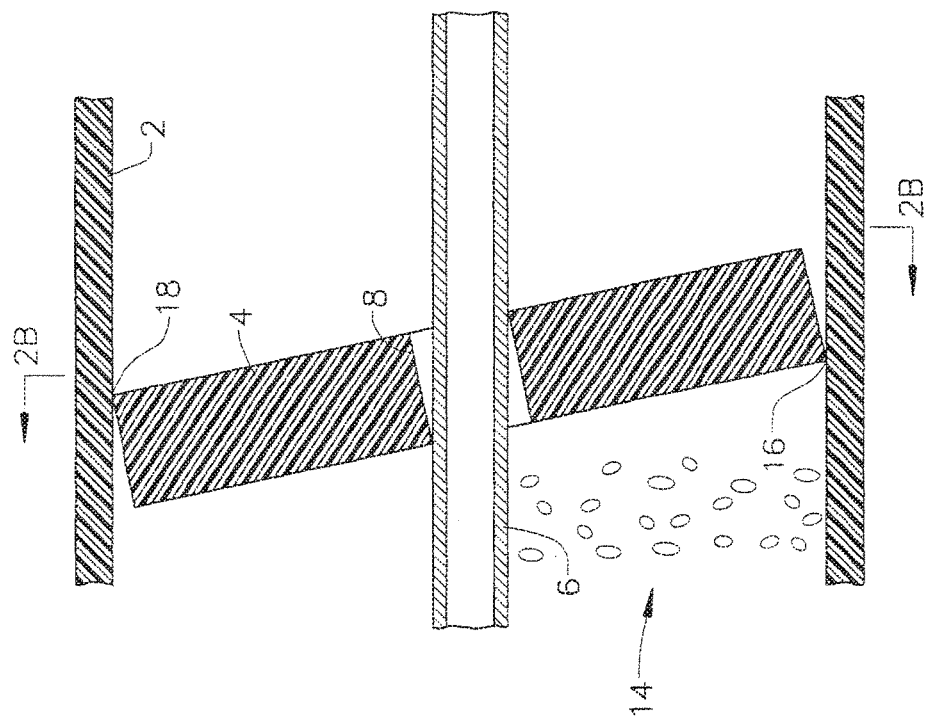
FIG. 2B is a transverse cross section taken along line 2B-2B of FIG. 2A.

Thus, when the processing tube is rotated to the decant position, the more dense red blood cells, illustrated at 14, that have accumulated below the disk exert a force against the bottom of the disk as they try to flow through the gap 12. This causes the disk 4 to rotate, as shown in FIGS. 2A and 2B, until a portion of the lower outer edge 16 of the disk and also the upper outer edge 18 engage the inner surface of the chamber 2. This engagement between the edge 16 of the disk and the interior of the chamber effectively forms a valve that prevents flow of the red blood cells, allowing decant of the plasma supernatant without contamination by red blood cells. It will be appreciated that this embodiment requires the transverse dimension of the disk between edges 16 and 18 to be greater than the internal diameter of the tube so that the edges engage the interior of the tube when tilted.

Figure 3B:
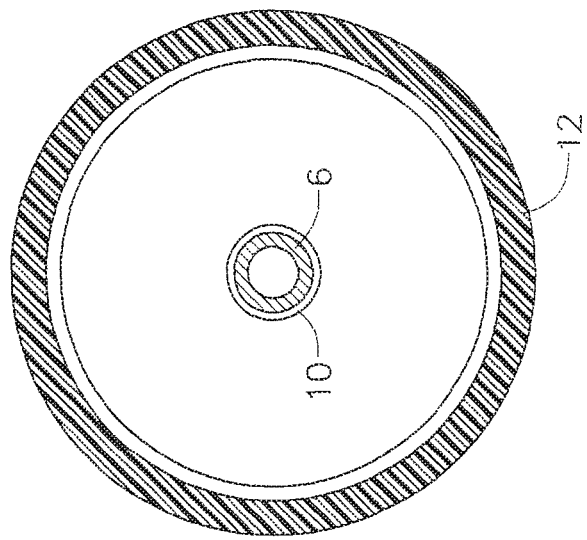
FIG. 3B is a transverse cross section taken along line 3B-3B of FIG. 3A.
Figure 3A:
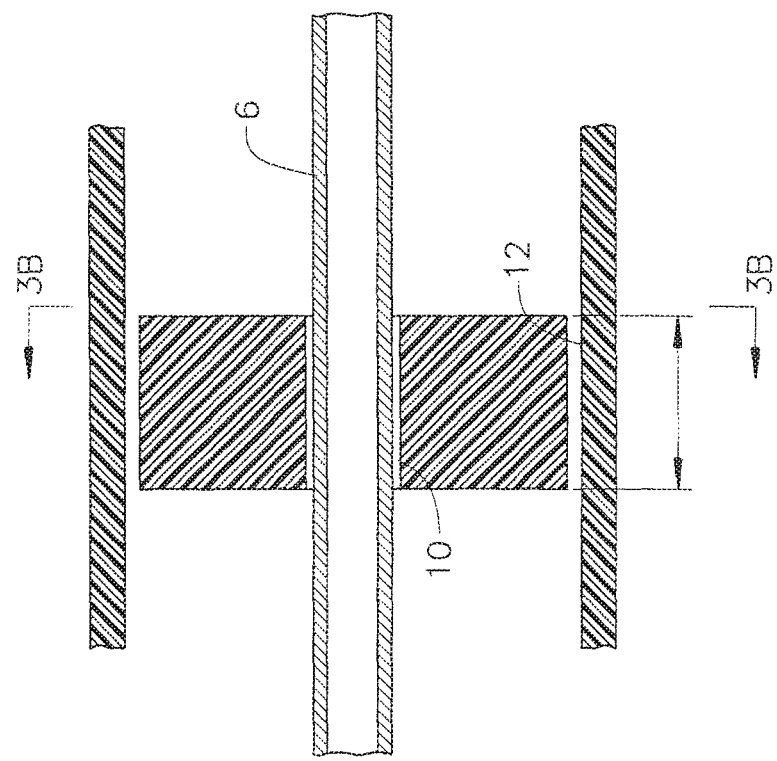
FIG. 3A is a longitudinal cross-section of a second embodiment of the invention.

A second embodiment is shown in FIGS. 3A and 3B. According to this embodiment, the gap 10 is made to be small whereby the disk does not rotate appreciably during decant, in contrast to the embodiment of FIGS. 1 and 2. It will be appreciated that an annular channel is formed by the gap 12, this channel having a width equal to the radial dimension of the gap and a length equal to the thickness of the disk at the edge. The rate of flow of a fluid through this channel is a function of the dimensions of the channel, and the dimensions of the disk of this embodiment are such that the red blood cells will not flow appreciably through the channel at 1 G. In the preferred embodiment, the width of the gap is about 0.005 inch to about 0.020 inch, and the length is about 0.1 inch to about 0.3 inch.

Thus, the components of the blood flow through the channel during centrifugation (i.e., at 1000G), but do not flow appreciably through the channel during decanting at 1 G. This allows the supernatant to be decanted without significant contamination by the red blood cells.

Figure 4:
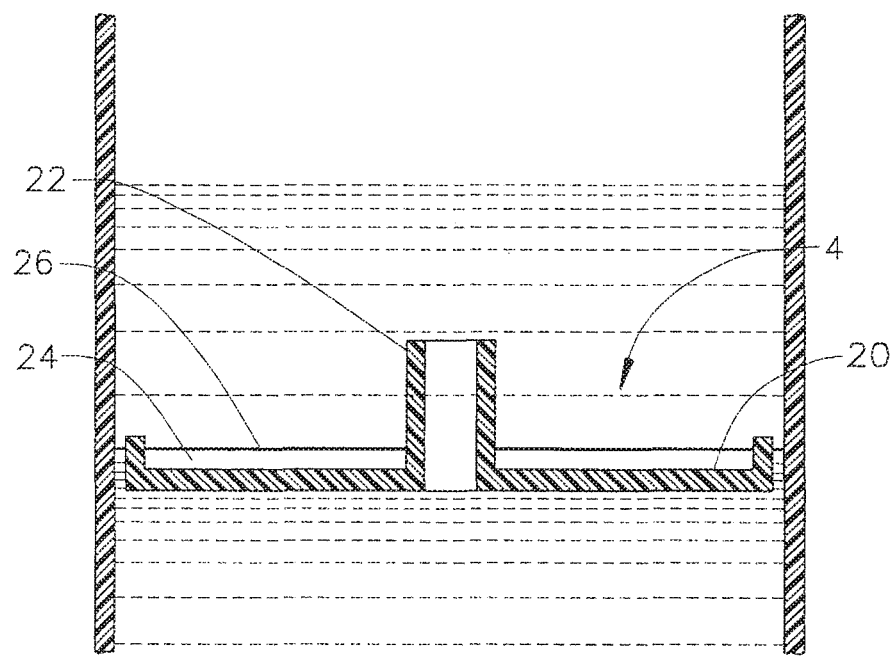
FIG. 4 is a longitudinal cross-section of a third embodiment of the invention.

FIG. 4 illustrates a preferred shape of the disk 4. In this embodiment, the top surface 20 of the disk is concave, preferably cylindrical, and the disk is provided with an elongated central portion 22. The specific gravity of the disk material is selected so that the concave surface 20 is located just below the interface. That is, the thickness of the outer edge, the length of the portion 22, and the specific gravity of the material are chosen so that the center of buoyancy of the disk is just above the concave surface, and that surface will be just below the interface 26 with red blood cells. This arrangement allows a small layer 24 of the red blood cells to form on the upper surface.

The layer of red blood cells 24 reduces the surface tension between the platelets at the interface 26 and the surface 20 of the disk and facilitates release of the platelets from the disk. This is important to ensure that all of the platelets are decanted, and the small amount of red blood cells that may be decanted along with the supernatant does not generally represent a significant contamination of the supernatant.

Modifications within the scope of the appended claims will be apparent to those of skill in the art.

We claim:

1. A system comprising:
    a container;
    a physiological fluid subjected to centrifugation in the container so as to provide an interface in the physiological fluid with red blood cells separated from at least one desired component of the physiological fluid; and
    a floating separator structure floating within the physiological fluid within the container, the floating separator structure having a shape and material that define a center of buoyancy of the floating separator structure in the physiological fluid within the container;
    wherein the floating separator structure includes: an outer periphery having an outer diameter smaller than an interior diameter of the container and having an axial height, an upwardly facing concave accumulating surface recessed lower than the axial height of the outer periphery and positioned radially inward from the outer periphery, and the center of buoyancy of the floating separator structure is located relative to the upwardly facing concave accumulating surface such that the upwardly facing concave accumulating surface is located just below the interface with the separated red blood cells to accumulate a small layer of red blood cells thereon while the outer periphery extends above the interface with the separated red blood cells.

2. The system according to claim 1, wherein the red blood cells reduce the surface tension between the at least one desired component and the accumulating surface, thereby facilitating release of the desired component from the accumulating surface.

3. The system according to claim 1, wherein the separator structure fits into the container such that a gap is formed between the outer periphery of the separator structure and the interior diameter of the container, the gap being of such a dimension that the red blood cells below said separator structure after separation do not flow appreciably through the gap at about 1G.

4. The system according to claim 1, wherein the accumulating surface of the separator structure is curved.

5. The system according to claim 1, wherein the accumulating surface of the separator structure is angled relative to a horizontal cross section of the container.

6. The system according to claim 1 wherein the separator structure is shaped such that its center of buoyancy is located above the accumulating surface of the separator structure.

7. The system according to claim 1, further comprising an elongated central portion extending from the upwardly facing concave accumulating surface of the separator structure.

8. The system of claim 7, wherein the elongated central portion has an axial height greater than the axial height of the outer periphery of the separator structure.

9. The system of claim 7, wherein the elongated central portion is joined with the upwardly facing concave accumulating surface of the separator structure, and the center of buoyancy of the floating separator structure is at least partially defined by the outer periphery, the elongated central portion, and the material of the floating separator structure.

* * * * *